(12) United States Patent
Bicchi et al.

(10) Patent No.: US 10,695,913 B2
(45) Date of Patent: Jun. 30, 2020

(54) UNDERACTUATED ROBOTIC HAND

(71) Applicants: UNIVERSITA' DI PISA, Pisa (IT); FONDAZIONE ISTITUTO ITALIANO DI TECNOLOGIA, Genoa (IT)

(72) Inventors: Antonio Bicchi, Massa (IT); Cosimo Della Santina, Pontedera (IT); Alberto Brando, Pontedera (IT); Cristina Piazza, Trapani (IT); Manuel Giuseppe Catalano, Pisa (IT); Giorgio Grioli, Pisa (IT)

(73) Assignee: UNIVERSITA' DI PISA, Genoa (IT)

( * ) Notice: Subject to any disclaimer, the term of this patent is extended or adjusted under 35 U.S.C. 154(b) by 171 days.

(21) Appl. No.: 15/772,368

(22) PCT Filed: Oct. 27, 2016

(86) PCT No.: PCT/IB2016/056468
§ 371 (c)(1),
(2) Date: Apr. 30, 2018

(87) PCT Pub. No.: WO2017/077429
PCT Pub. Date: May 11, 2017

(65) Prior Publication Data
US 2018/0311827 A1   Nov. 1, 2018

(30) Foreign Application Priority Data
Nov. 2, 2015   (IT) ................ UB2015A5328

(51) Int. Cl.
A61F 2/54   (2006.01)
A61F 2/58   (2006.01)
(Continued)

(52) U.S. Cl.
CPC .......... B25J 15/0009 (2013.01); A61F 2/583 (2013.01); A61F 2/586 (2013.01); A61F 2/68 (2013.01);
(Continued)

(58) Field of Classification Search
CPC .... A61F 2/54; A61F 2/58; A61F 2/586; B25J 15/02; B25J 15/08; B25J 15/0233
See application file for complete search history.

(56) References Cited

U.S. PATENT DOCUMENTS 4,834,761 A   5/1989   Walters
4,955,918 A   9/1990   Lee
(Continued)

FOREIGN PATENT DOCUMENTS

CN   103565562 A   2/2014
FR   588 700 A   5/1925
WO   2013/185231 A1   12/2013

*Primary Examiner* — Bruce E Snow
(74) *Attorney, Agent, or Firm* — Vorys, Sater, Seymour and Pease LLP; Anthony Venturino (57) ABSTRACT

Provided is a robotic hand which includes a palm, a plurality of phalanges adapted to reproduce a plurality of fingers, and an actuating mechanism. The actuating mechanism may include a first pulley located at each hinge and bound to the first element, second pulleys located at each of the hinges and bound to the second element, a single cable running in all of the pulleys and a motor adapted to act on the cable by controlling the rotation of the phalanges.

11 Claims, 5 Drawing Sheets

(51) Int. Cl.

| | |
|---|---|
| *B25J 15/00* | (2006.01) |
| *B25J 15/02* | (2006.01) |
| *B25J 15/08* | (2006.01) |
| *A61F 2/68* | (2006.01) |
| *A61F 2/70* | (2006.01) |

(52) U.S. Cl.
CPC ......... *B25J 15/0233* (2013.01); *B25J 15/086* (2013.01); *A61F 2002/704* (2013.01)

(56) References Cited

U.S. PATENT DOCUMENTS

| | | | |
|---|---|---|---|
| 6,668,678 B1 | 12/2003 | Baba et al. | |
| 6,896,704 B1* | 5/2005 | Higuchi | A61F 2/583 623/25 |
| 9,016,744 B2* | 4/2015 | Starkey | A61F 2/583 294/106 |
| 10,426,636 B2* | 10/2019 | Mandl | A61F 2/586 |
| 2014/0097631 A1 | 4/2014 | Ciocarlie et al. | |
| 2017/0049583 A1* | 2/2017 | Belter | A61F 2/583 |

* cited by examiner

UNDERACTUATED ROBOTIC HAND

The object of the present invention is a robotic hand of the type specified in the preamble of the first claim.

In particular, the object of the present invention is a robotic hand capable of reproducing the movements of a human hand and, precisely, the grasping movements of a human hand.

The human hand is able to perform a wide range of movements and, in particular, to grasp objects of various sizes by adapting the arrangement of the fingers to the object to be grasped.

To emulate these movements, the anthropomorphic robotic hands currently in use have, at each joint, a motor mutually moving two elements, for example two phalanges, and a motor control sensor.

In order to allow the robotic hand to be controlled from the outside, each motor and each sensor are connected, via cables, to a control board and to a power supply system.

The above mentioned prior art has a few major drawbacks.

A first drawback is that, in order to emulate the large number of degrees of freedom of the human hand, the currently known robotic hands require the same number of motors and control sensors and, therefore, are complex to build.

This aspect is further emphasised by the need to use a large number of cables to connect each motor and each sensor to the control board and to the power supply system.

Such a large number of sensors, motors and cables makes it almost impossible to obtain a robotic hand having dimensions comparable to those of a human hand.

Thus, a further drawback is due to the complexity of management and control of a known robotic hand, caused by the need to control a large number of components simultaneously.

In this context, the technical task underlying the present invention is to devise a robotic hand which is capable of substantially obviating the above-mentioned drawbacks.

Within the scope of said technical task, a major object of the invention is to provide a robotic hand which is simple to make and capable of achieving any grasping pose. Another major object of the invention is to provide a robotic hand that is simple to manage and control.

A further object of the invention is to develop a robotic hand with small dimensions. The technical task and the specified objects are achieved by means of a robotic hand as claimed in the appended claim 1.

Preferred embodiments are set forth in the dependent claims.

The features and advantages of the invention will be apparent from the detailed description of a preferred embodiment of the invention, with reference to the accompanying drawings, in which.

In the present document, the measures, values, shapes and geometric references (such as perpendicularity and parallelism), when associated with terms such as "about" or with other similar terms such as "almost" or "substantially", are to be understood as contemplating the possibility of measurement errors or inaccuracies due to production and/or manufacturing defects and, especially, contemplating the possibility of a slight difference in the value, measure, shape or geometric reference with which it is associated. For example, these terms, if associated with a value, preferably indicate a difference of not more than 10% of the value itself.

Furthermore, when used, terms such as "first", "second", "higher", "lower", "main" and "secondary" do not necessarily identify an order, a priority relationship or a relative position, but can simply be used to distinguish more clearly the different components from each other.

With reference to the aforementioned figures, the robotic hand according to the invention, as a whole, is indicated by the numeral 1.

It is preferably capable of reproducing an anthropomorphic hand and, more preferably, a human hand.

The robotic hand 1 is suitable to be used in both robotic and prosthetic applications.

The robotic hand 1 comprises a palm 2 of the robotic hand 1 and a plurality of phalanges designed to reproduce the fingers, each defining its own preferred development trajectory.

In particular, the robotic hand 1 comprises a number of phalanges so as to allow said robotic hand 1 to have five fingers. More in particular, the robotic hand 1 comprises, for each finger, at least one phalanx 3a proximal to the palm 2; a phalanx 3b distal to the palm 2 and defining the fingertip. Still more in particular, each finger of the robotic hand 1 is composed of three phalanges, i.e. two proximal phalanges 3a, suitably positioned one after the other along the finger's preferred development trajectory, and a distal phalanx 3b.

In order to allow the robotic hand 1 to replicate the movements of a human hand, the robotic hand 1 comprises a plurality of hinges 4, each of which hinging a first element, coinciding with one of the phalanges 3a, 3b, to a second element, coinciding with one among the palm 2 and one of the phalanges 3a, 3b different from that forming said first element.

Precisely, a hinge 4 may be interposed between a proximal phalanx 3a and the palm 2; between a proximal phalanx 3a and a distal phalanx 3b; and/or between two proximal phalanges 3a.

More precisely, the robotic hand 1 comprises fifteen hinges 4 arranged as follows: five interposed between a proximal phalanx 3a and the palm 2, five between adjacent proximal phalanges 3a, and five between the proximal phalanx 3a and the adjacent distal phalanx 3a.

Each hinge 4 is adapted to define a mutual rotation axis between said first element and said second element preferably substantially perpendicular to the preferred development trajectory.

Each hinge 4 comprises two, suitably toothed, curved surfaces 41, one of which being integral with the first element and another with the second element and adapted to reciprocally engage and slide, allowing for rotation between the first and the second element; and suitably, elastic means 42 adapted to tighten said elements relative to one another, ensuring contact between the curved surfaces 41.

The elastic means 42 are adapted to exert an attraction force between the first and the second element.

It is noted that the elastic means 42, as described in greater detail below, work in opposition to a closure of the hand, i.e. to an angular approach of the phalanges 3a and 3b, and therefore to the achievement of a grasping pose, thereby facilitating the spreading apart of the phalanges 3a and 3b.

They comprise at least one, preferably two, suitably closed wire(s) connecting the first element to the second element so as to oppose to their moving away from each other. Thus, said elastic means 42 connect two adjacent phalanges 3a and/or 3b and/or a proximal phalanx 3a to the palm 2.

Said closed elastic loop or said elastic segment is made of elastic material and, in detail, of elastomer material.

Each hinge 4 lastly comprises a stopper 43 adapted to limit the angle of divergence between the first and the second element.

The stopper 43 comprises a first tooth 431 protruding from the first element and a second tooth 432 protruding from the second element and suitable to abut with the first tooth 431, limiting the rotation between the first and the second element.

In order to control the movement and, precisely, the rotation of the phalanges 3a and 3b on said hinges 4, the robotic hand 1 comprises at least one actuating mechanism 5.

In particular, the hand 1 may comprise a single actuating mechanism 5 as shown in FIGS. 1b, 1d, 2b and 2d. Alternatively, it comprises two actuating mechanisms 5 capable of working and, in detail, of being controlled independently of each other. In a further alternative, the robotic hand 1 may comprise more than two actuating mechanisms 5.

The actuating mechanism 5 comprises, at each hinge 4, at least a first pulley 51 bound to the first element and at least a second pulley 52 bound to said second element; a single cable 53 running in all of the pulleys 51 and 52; at least one motor 54 adapted to act on the cable 53 by controlling the rotation of the phalanges 3a and/or 3b.

Conveniently, the actuating mechanism 5 can additionally comprise a control unit in data exchange connection with the at least one motor 54, allowing the operator (identifiable with a human operator or a robot\computer) to control the at least one motor 54 and, consequently, the robotic hand 1, and a power supply of said at least one motor.

The first pulley 51 of a hinge faces the second pulley 52 of the same hinge. Therefore, between the pulleys 51 and 52 of a hinge there are no components in contact with the cable 53, so that the portion of the cable 53 subtended between said pulleys 51 and 52 has substantially the same tension.

Preferably, at each hinge 4, the actuating mechanism 5 comprises two first pulleys 51 bound to the first element and two second pulleys 52, each of which is bound to the second element and suitably facing a first pulley 51.

Advantageously, at least one of the first 51 and second pulleys 52 has a different friction, causing tension drops in the single cable 53, which are different from one another, so that the single cable 53 comprises subtended sectors between the pulleys 51 and 52, which have a non-homogeneous tension, giving different actuation forces to the elements and consequently different mutual rotation speeds between said elements. In particular, at at least one hinge 4, the actuating mechanism 5 comprises pulleys 51 and 52 having different frictions.

The expression having different frictions means that the pulleys 51 and/or 52 can have different coefficients of, suitably rotational, friction on the cable 53 and/or on the element with which they are engaged. Advantageously, the pulleys 51 and/or 52 have different friction coefficients with respect to the element with which they are engaged so that at least part of the pulleys 51, 52 transmit, to the element with which they are associated, a torque suitably different from that transmitted by one or more of the other pulleys 51 and/or 52 to the corresponding element, causing different mutual rotation speeds between the elements.

Advantageously, it is noted that the presence of pulleys 51 and/or 52 with different frictions allows for the occurrence of a tension drop on the cable 53 and, hence, for the tension on the cable 53 to be lower at the last contact point (i.e. the separation point) on the pulley compared to that possessed by the cable 53 at the first contact point of the cable 53 on the same pulley.

In particular, this different friction is such that the pulleys 51 and 52 mutually cause different tension drops on the cable 53. Therefore, the cable 53 comprises sectors subtended between the pulleys 51 and 52, at least momentarily (preferably always) with a non-homogeneous tension, giving different actuation forces to said elements and different mutual rotation speeds between the elements and, therefore, to the phalanges 3a and 3b.

and thus transmit a distinct torque to the element, giving mutually different forces transmitted to said elements and, therefore, different mutual rotation speeds between said elements.

The different friction is such that the cable comprises sectors subtended between the pulleys, at least momentarily with a non-homogeneous tension, giving different actuation forces to said elements and different mutual rotation speeds between said elements.

Therefore, the pulleys 51 and/or 52 with different frictions are subjected by the cable 53 to mutually different torques and, therefore, transmit a different torque to the corresponding element.

Three of some of the possible examples wherein the pulleys 51 and/or 52 have different friction coefficients with respect to the element with which they are engaged are described below only by way of non-limiting example. Said three examples are mutually implementable.

In a first example, the pulleys 51 and 52 may have different frictions since they are bound to the first and second elements partly in a firm way and partly in a labile way via, for example, bearings and bearing shells interposed between said pulleys and said elements.

In a second example, the pulleys 51 and 52 may have different frictions since they are bound to the first and second elements in a labile way via different bearings/bearing shells so as to vary the friction coefficient between the pulleys 51 and 52 and said elements.

In a third example, the pulleys 51 and 52 of a robotic hand 1 may have different frictions since they are at least partially made of different materials so as to define a different rotational friction coefficient with respect to the element with which they are bound.

Alternatively or additionally, as anticipated above, the pulleys 51 and 52 may have different frictions with respect to the cable 53 as described in the fourth example.

In a fourth example, the pulleys 51 and 52 may have different frictions since they have different radii so as to vary the length of the race in contact with the cable 53 and, thus, the rotational friction coefficients.

It is noted that the four examples shown above may be combined with each other. Therefore, the robotic hand 1 can have pulleys 51 and/or 52 integral with the corresponding element; pulleys 51 and/or 52 labily bound to the corresponding element with different bearing shells/bearings; pulleys 51 and/or 52 made of different materials; and/or pulleys 51 and/or 52 with different radii.

The pulleys 51 and 52 may be made of a material selected from steel, PVC, polymeric materials, aluminium and ceramic.

The pulleys 51 and 52 associated with a same hinge 4 define axes substantially parallel and, particularly, substantially coincident with each other. In particular, the pulleys 51 and 52 of a finger have axes substantially parallel to each other and substantially perpendicular to the preferred development trajectory of the finger itself.

The single cable 53 advantageously connects all the pulleys 51 and 52 of all the phalanges 3a and 3b and, suitably, of the palm 2. In detail, said single cable 53 is in contact with all the pulleys 51 and 52 of all the phalanges 3a and 3b and, suitably, of the palm 2. More in detail, said single cable 53 is arranged to run in all the pulleys 51 and 52 of all the phalanges 3a and 3b and, suitably, of the palm 2.

The cable 53 is able to run individually inside all the pulleys 51 and 52, i.e. is adapted to contact only one of each pulley 51 and 52 in the robotic hand 1.

It is made of a material having an elastic coefficient at least equal to 50 Gpa and, specifically, to 100 Gpa. It is made of a material selected from steel, PVC and a synthetic fibre such as, preferably, Dyneema (Gel Spun Polyethylene).

The cable 53 is open and has both the two ends engaged with the at least one motor 54.

The actuating mechanism 5 comprises at least two motors 54, suitably exactly two motors, each of which is engaged at one end of the cable 53 so as to be able to selectively act, appropriately on the basis of a command of the control unit which can be given by the operator, on the cable 53, exerting thereon either two mutually equal torques/forces and, therefore, two mutually identical tensions at the two ends of the cable 53; or two distinct torques/forces and, thus, two different (in modulus and/or direction) tensions at the two ends of the cable 53. In some cases, the ability of having different tensions at the two ends of the cable 53 can be equally obtained with a single motor 54 engaged, via distinct kinematic mechanisms, at the two ends of the cable 53, so as to be able to apply to the two ends of the cable 53 tensions that can be equal to each other or different from each other.

The control unit is able to control the two motors by varying the tension that each engine applies to the cable 53, so as to change the mutual rotation speeds between the elements (in particular the phalanges 3a and 3b) and, thus, the pose that can be assumed by the robotic hand 1. It can therefore command the motors 54 to apply to the cable 53 tensions equal in modulus and direction and/or tensions different in at least one of the modulus and the direction.

Said tensions, according to the command given to the motors 54, can then be either substantially equal to each other, i.e. equally orientated and with the same modulus, so as to vary the tension of the cable 53 without said cable 53 running in the pulleys 51 and 52, or different from each other, i.e. differently orientated and/or with a different modulus so that the cable 53 can run in the pulleys 51 and 52.

The motors 54 are preferably electrical. In particular, they are servomotors i.e. motors equipped with a control board through which the motors themselves can be controlled.

The motors 54 are integral with the palm 2.

In order to adjust and monitor the tension applied to the cable 53, thus the torque/output force exiting the motor 54, the mechanism 5 may further comprise, for each motor 54, a preferably magnetic, position sensor 55, adapted to measure the position and therefore, the angular velocity of the output shaft of a motor 54.

In order to ensure contact of the cable 53 with the first pulley 51, the cable 53 is adapted to define an output angle from the first pulley 51, preferably at least equal to 30° and, in particular, at least equal to 45°.

Said output angle is defined by the inclination of the cable 53 with respect to the lying plane 5a of adjacent pulleys 51 and 52 at the last contact point (i.e. the separation point) of the cable 53 on the same pulley 51.

This plane 5a is for the lying of the axis of a first pulley 51 and of the axis of a second pulley 52 located at adjacent hinges 4 and, precisely, associated with the same, suitably proximal, phalanx 3a. It should be noted that each proximal phalanx 3a can define, for the axes of the pulleys 51 and 52 therewith associated, its own lying plane 5a distinct from that of the adjacent phalanx.

Similarly, in order to ensure contact of the cable 53 with the second pulley 52, the cable 53 is adapted to define an input angle in the second pulley, preferably at least equal to 30° and, in particular, at least equal to 45°.

Said input angle is defined by the inclination of the cable 53 with respect to the lying plane 5a of the axes of the pulleys 51 and 52, at the first contact point of the cable 53 on the same pulley 51.

It is noted that the contact between the cable 53 and each pulley 51 and 52 can be achieved in several ways as known to those of skill in the art and, for example, can be obtained by arranging the cable 53 so that it contacts the first pulley 51 of a hinge 4 on the opposite side of the second pulley 52 of the adjacent hinge 4 with respect to the lying plane 5a.

Preferably, the contact between the cable 53 and each pulley 51 and 52 was designed by providing an actuating mechanism 5 comprising at least one drive 56 for the cable 53 adapted to tilt the cable 53 with respect to the lying plane 5a and, therefore, to define said inlet angle and/or said output angle.

In particular, the actuating mechanism 5 comprises a plurality of drives 56, each of which is interposed between two adjacent pulleys 51 and 52, more particularly, between a first pulley 51 of a hinge 4 and a second pulley 52 located at the adjacent hinge 4 and, even more particularly, between the first pulley 51 and the second pulley 52 of a proximal phalanx 3a.

Figure 3:
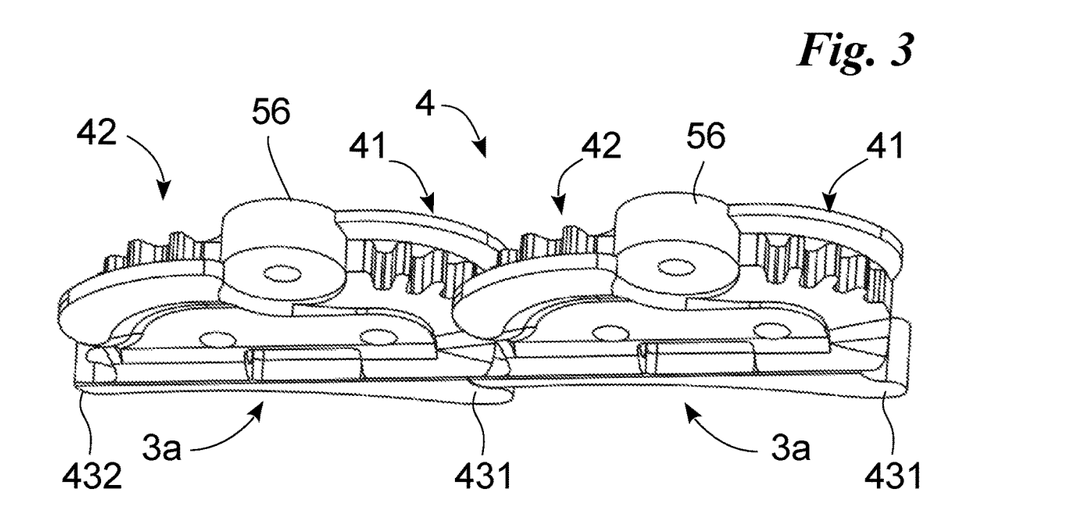
FIG. 3 shows a detail of the robotic hand according to the invention.
Figure 4:
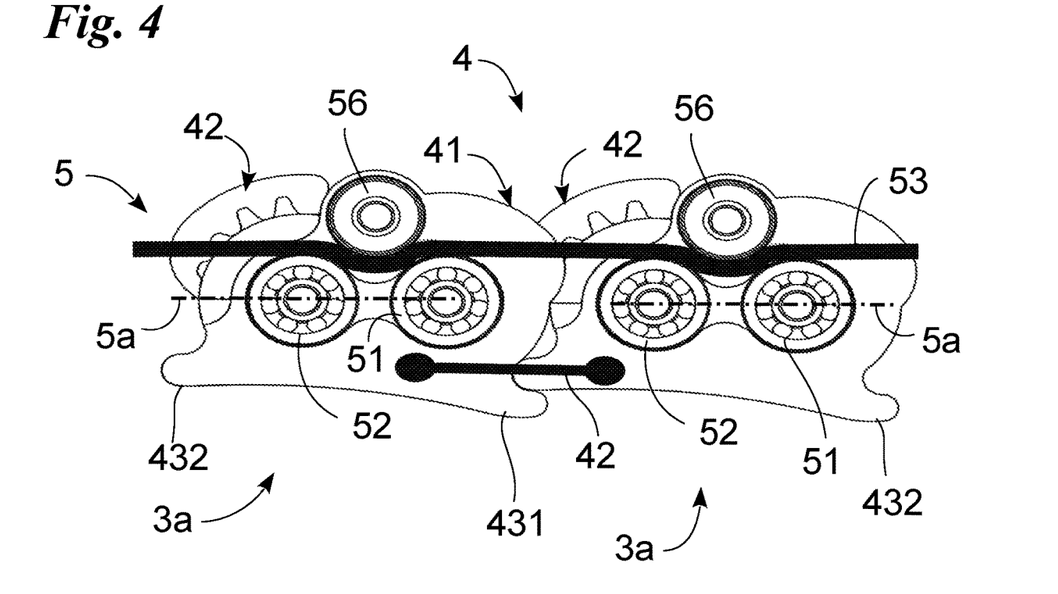
FIG. 4 shows a second view of the detail in FIG. 3.

Each drive 56 is identifiable by a pin, a sheave or other similar element interposed between adjacent pulleys 51 and 52 so as to define a surface of contact with the cable 53 opposite, with respect to the same drive 56, to that between the same cable 53 and the pulleys 51 and 52. Consequently, the cable 53, passing from a first pulley 51 to a second pulley 52 through the drive 53 defines a substantially U-shaped path as shown in FIG. 3.

For example, in the case of the axis of the drive 56 being equidistant from the axes of the pulleys 51 and 52, and the radius of the drive 56 and of the pulleys 51 and 52 being equal, the distance between the axis of the drive 56 and the lying plane 5a is at least $1/2\sqrt{3}$ and, more advantageously, at least equal to half the distance between the axes of the pulleys 51 and 52.

Similar to the pulleys 51 and 52, each drive 56 can have a different friction. Therefore, in a robotic hand 1, there may be drives having different radii, made of a different material and/or having a different binding with respect to the phalanges 3a. Each of the phalanges 3a and 3b comprises at least one support 31 for at least one of said pulleys 51 and/or 52 and, in particular, for at least two pulleys 51 and/or 52. The support 31 defines a housing seat suitable to at least partially accommodate the pulleys 51 and/or 52. In particular, it has a U-profile whose edges are internally engaged by the pulleys 51 and/or 52.

The support 31 can be made of a material selected from steel, PVC, aluminium.

One or more curved surfaces 41 are formed on the support 31.

At least one of the first tooth 431 and the second tooth 432 protrudes therefrom, suitably from opposite sides along the trajectory of a finger.

In summary, for clarity, each proximal phalanx 3a comprises a support 31 and, engaged with it, at least a first pulley 51, at least a second pulley 52, at least two curved surfaces of the hinge 4 and, conveniently, at least one drive 56. Preferably, each proximal phalanx 3a comprises two first pulleys 51, two second pulleys 52, four curved surfaces 41 and, conveniently, two drives 56.

Additionally, each proximal phalanx 3a may comprise at least a first tooth 431 and at least a second tooth 432 protruding from the support 31, suitably from opposite sides along the trajectory of a finger.

Each distal phalanx 3b comprises a support 31 and, engaged with it, at least a first pulley 51, at least a curved surface of the hinge 4 and, conveniently, at least a second tooth 432. Preferably, a distal phalanx 3b comprises two first pulleys 51, two curved surfaces of the hinge 4, two second teeth 432.

Advantageously, each distal phalanx 3b comprises return means adapted to allow the output cable 53 exiting a first pulley 51 to enter the other first pulley 51.

The return means are identifiable by a sheave having an axis substantially perpendicular to the axis of the pulleys 51 and 52.

Similar to the pulleys 51 and 52 and, possibly to the drive 56, the return means can have different frictions. Therefore, in a robotic hand 1, there may be drives having different radii, made of a different material and/or having a different binding with respect to the phalanges 3a.

The palm 2 comprises a base body 21 with which at least five and, in particular, ten second pulleys 52, the at least one motor 54, preferably two motors, and tensioning means identifiable by supplementary pulleys or other similar means suitable to ensure correct tensioning of the cable 53, are engaged.

Preferably, the palm 2 may comprise at least five and, in particular, ten first teeth 431 protruding from the base body 21.

The operation of a robotic hand, described above as regards structure, is as follows. Initially, the fingers of the robotic hand 1 are outstretched, i.e. the phalanges 3a and 3b are mutually spread apart by an angle such as to bring the teeth 431 and 432 in contact with each other.

When grasping an object with all the fingers, the operator places the object on the palm 2, and, via the control unit, commands the motors 54 to exert an equal torque, and therefore, an equal force on the cable 53 by changing the tension on the cable itself.

This force varies, and specifically, increases evenly the tension acting on the cable 53 by imposing on each pulley 51 and/or 52 a torque which depends on the friction, and conveniently, by the radii of all the pulleys 51 and 52 of the hand 1. Consequently, each pulley 51 and/or 52 transmits a different torque to the corresponding phalanx 3a and/or 3b, causing a different rotation speed around each hinge 4. Therefore, the robotic hand 1 closes with different speeds in the phalanges 3a and 3b.

Consequently, the curved surfaces 41 slide mutually causing rotation of the phalanges 3a and 3b, coming into contact with the object.

The grasp is completed when the torque on the pulleys 51 and 52 is equal to that exerted by the object on the phalanges 3a and 3b, and therefore the phalanges stop.

It is noted that the elastic means 43 work in opposition to the closure of the hand 1, and therefore to the angular approach between adjacent phalanges 3a and 3b. Accordingly, a possible tension drop on the cable 53, for example, due to deactivation of the motors 54 or to a reduction in the output torque, allows the elastic means 42 to make the hand 1 go back to the initial position or at least partially go back to said initial position.

Suppose now you want to grasp an object with only some of the five fingers or making some fingers get to the object before others.

In this case, the operator, after placing the object on the palm 2, commands the motors 54, via the control unit, to exert different torques, and therefore different forces on the cable 53 (a condition obtainable by commanding the motors 54 to move in the opposite direction, by imposing the same direction but a different modulus, or by leaving one motor 54 inactive).

Because of this different force exerted at its ends, the cable 53 causes rotation of the pulleys 51 and 52, which, by having different frictions (suitably also different radii), are subjected to torques different from each other as they are proportional to said friction and to the radii of the pulleys 51 and/or 52. This difference in torque/tension is such that the pulleys 51 and 52 transmit distinct torques to the phalanges 3a and 3b, which, thus, move with different speeds. Therefore, this results in distinct movements of the fingers as shown in the sequence depicted in FIGS. 2a-2d.

The invention comprises a new design process for a robotic hand 1 structurally and functionally described above.

This design process is characterized by a selection of frictions of the first pulleys 51 and of the second pulleys 52. This selection is made in such a way that the frictions are determined so that the pulleys 51 and/or 52 cause tension drops in the single cable 53, which are different from one another, and so that the single cable 53 comprises subtended sectors between the pulleys 51 and/or 52 (suitably between adjacent pulleys 51 and 52), which have a non-homogeneous tension. Therefore, the cable 53, when subject to tension by the motor 53 (particularly by the at least two motors, preferably two, and appropriately with tensions at the ends which are identical and/or different) and, in particular, subject to different tensions applied by the two motors 53, shows sectors having different tensions which give, by means of the pulleys 51 and/or 52, different actuation forces to the elements, and consequently different mutual rotation speeds between said elements.

The invention allows for significant advantages.

A first major advantage is the ease of construction of the robotic hand 1.

In fact, with only one cable 53 controlled by the at least one motor 54, the robotic hand 1 is capable of controlling the movement of each single phalanx 3a and 3b, and therefore of optimally reproducing a grasping pose independently of the shape/size of the object to be grasped.

This possibility is maximized in the case of a robotic hand 1 with two motors 54. In fact, in this case it is possible to move differently the various phalanges 3a and 3b, so as to achieve an increased plurality of grasping poses, and therefore, reproduce a high number of poses of the human hand even more accurately.

This aspect has been innovatively obtained via pulleys 51 and 52 having different frictions. In fact, in contrast with what was previously pointed out in earlier studies, the use of friction, and hence the adjustment, in the design stage, of suitable pulleys 51 and 52 having different frictions with respect to the elements with which they are connected allows for having, at the pulleys 51 and 52, different tension drops on the cable 53, and hence different torques transmitted by the same pulleys 51 and 52 to the first and second elements.

Another advantage is therefore due to the fact that, the robotic hand 1, by simply changing the speeds/output torques exiting the motors 54, is able to change the speeds of the individual phalanges 3a and 3b, and thus modify the grasping pose, therefore providing for grasps with all fingers or with only some of them that are folded on the object.

This advantage is further increased by the fact that by adjusting, and in particular, by making the radii of the pulleys 51 and 52 different, it is possible to vary the torque transmitted to the phalanges 3a and 3b and, consequently, modify the speed with which said phalanges 3a and 3b rotate by opening or closing the robotic hand 1. This advantage is particularly evident in the case of two motors where, due to possible operation of the motors 54 with different speeds/output torques, this difference in radii, thanks also to the variation of the tension on the cable 53, results in a variation, suitably directly proportional to the variation of the radius, of the torque transmitted by the cable 53 to the individual pulley 51 or 52. In fact, this aspect is due to the fact that larger-radius pulleys 51 and 52 have a greater portion of the cable 53 in contact with the pulley 51 and/or 52, which results in a higher static friction between said cable and said pulley, and therefore a greater torque transmitted.

It is noted that another advantage is due to the fact that the introduction of a determined friction coefficient, localized in the pulleys 51 and 52 or distributed along the path, causes the cable 53, by crossing the pulleys 51 and 52 along its path, to induce an uneven distribution of the tension along the cable itself. Therefore, through appropriate selection of the friction coefficients combined with a particular selection of the torques generated by the two motors 54, any effective tension may be applied to the cable 53, and hence, it is possible to differentiate from one another the actual torques on the phalanges 3a and 3b, and therefore the closure.

In summary, the effects resulting from the presence of two motors, which can be controlled by the control unit independently of each other, on the distribution of the tension on the cable 53 entail an actual multiplicity of closure morphologies, and this gives the robotic hand 1 innovative and increased handling capabilities.

To better illustrate this advantage, a few possible basic configurations for using the robotic hand 1 are set forth for illustrative purposes.

Figure 1A:
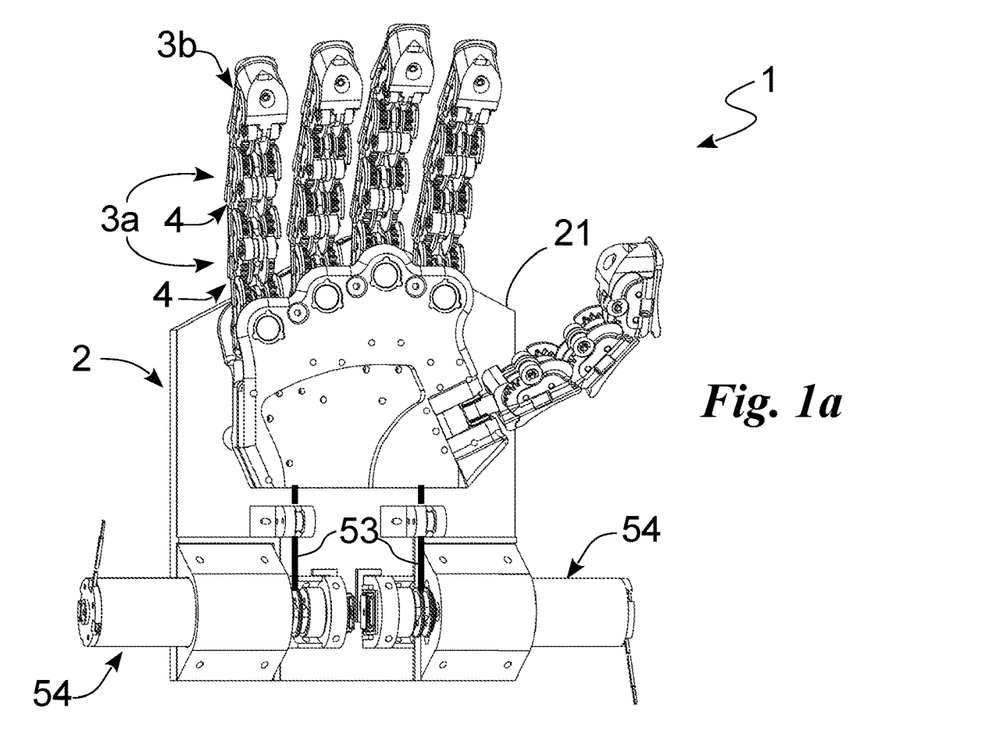
FIGS. 1a-1d show an operation sequence of the robotic hand according to the invention.
Figure 1B:
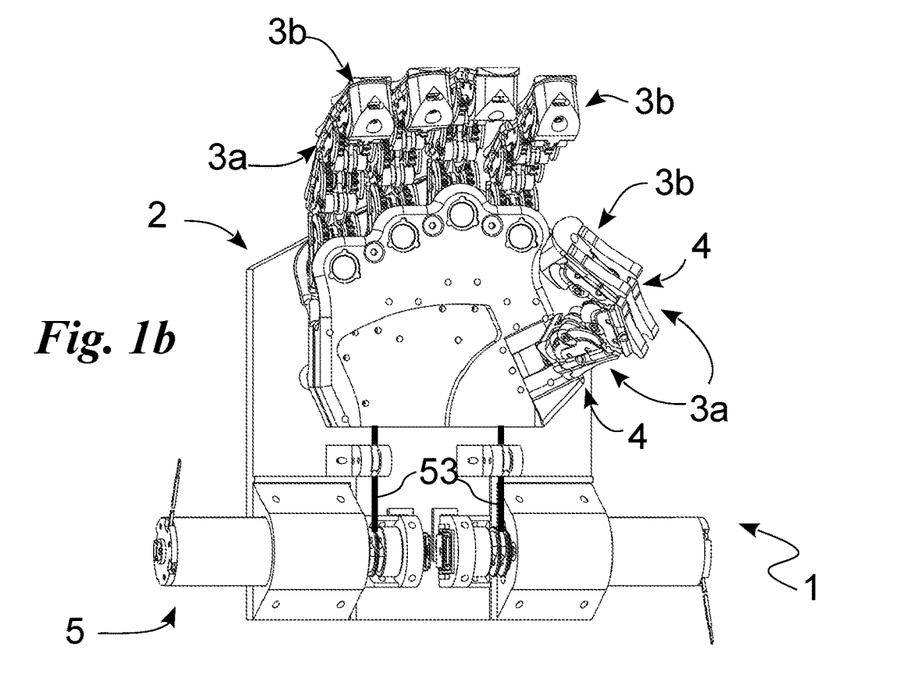
Figure 1C:
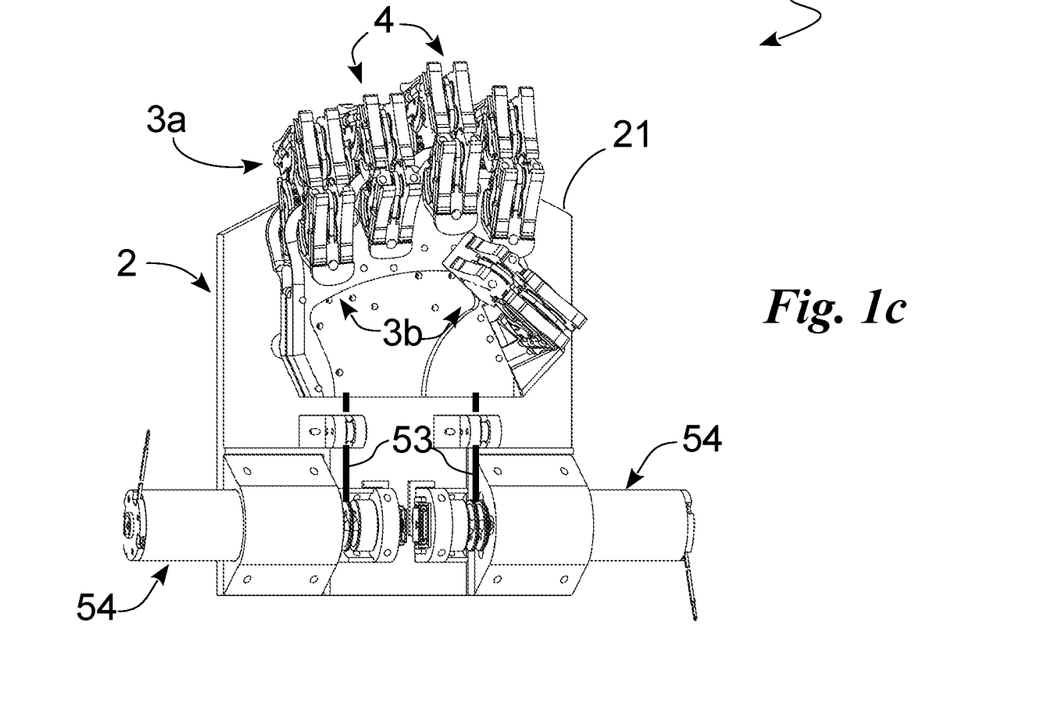
Figure 1D:
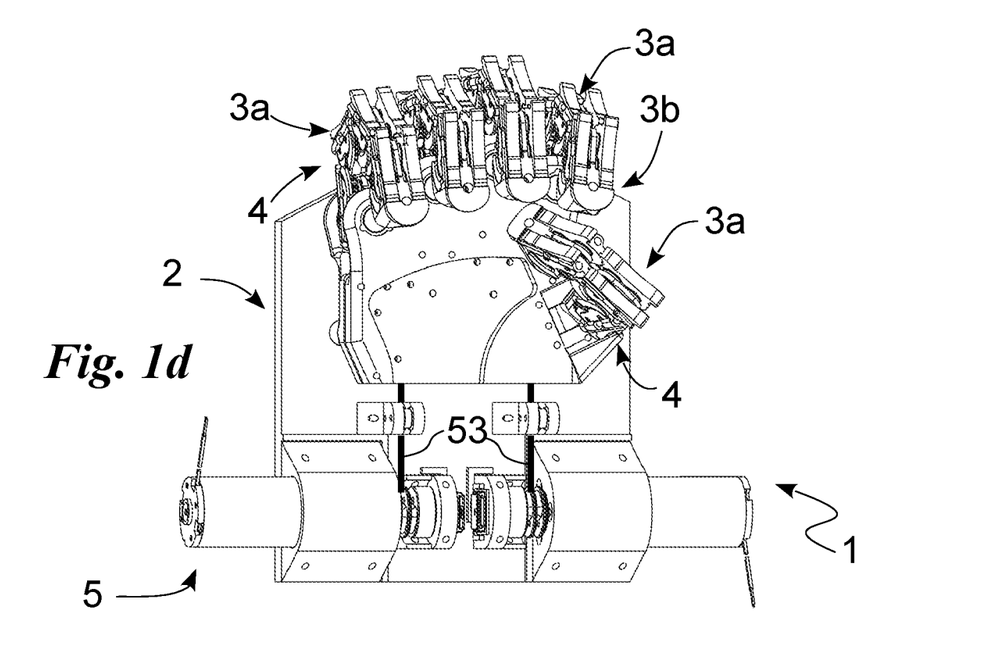

In a first example, both motors 54 are actuated in a concordant way. Consequently, in the robotic hand 1, the movement of the fingers is not sequential, but simultaneous (FIGS. 1a-1c), defining a final configuration with a closure as that shown in FIG. 1c.

Figure 2A:
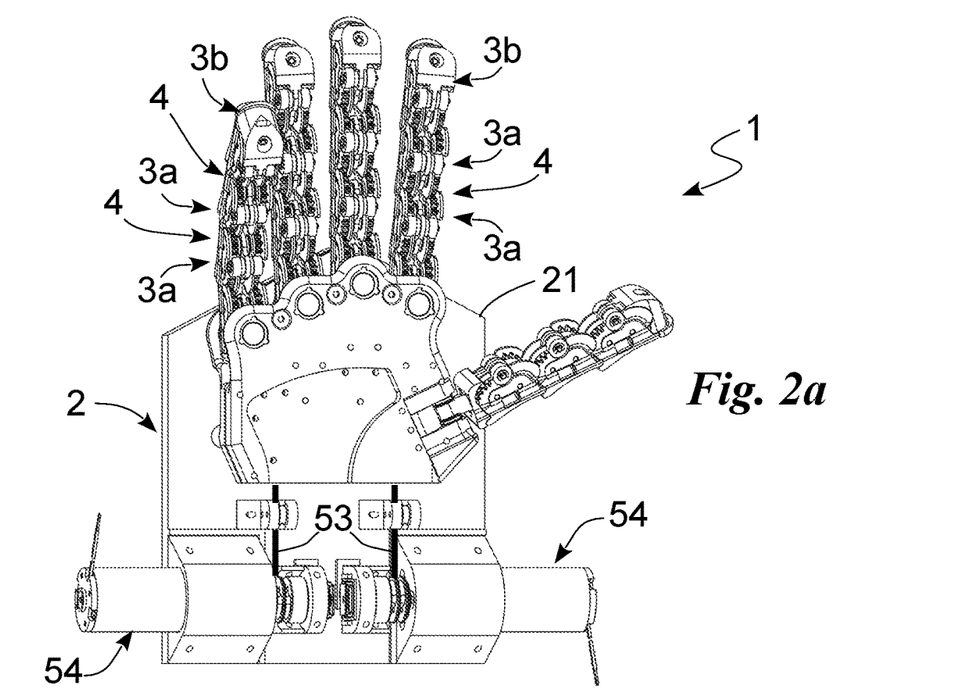
FIGS. 2a-2d illustrate a further operation sequence of the robotic hand.
Figure 2B:
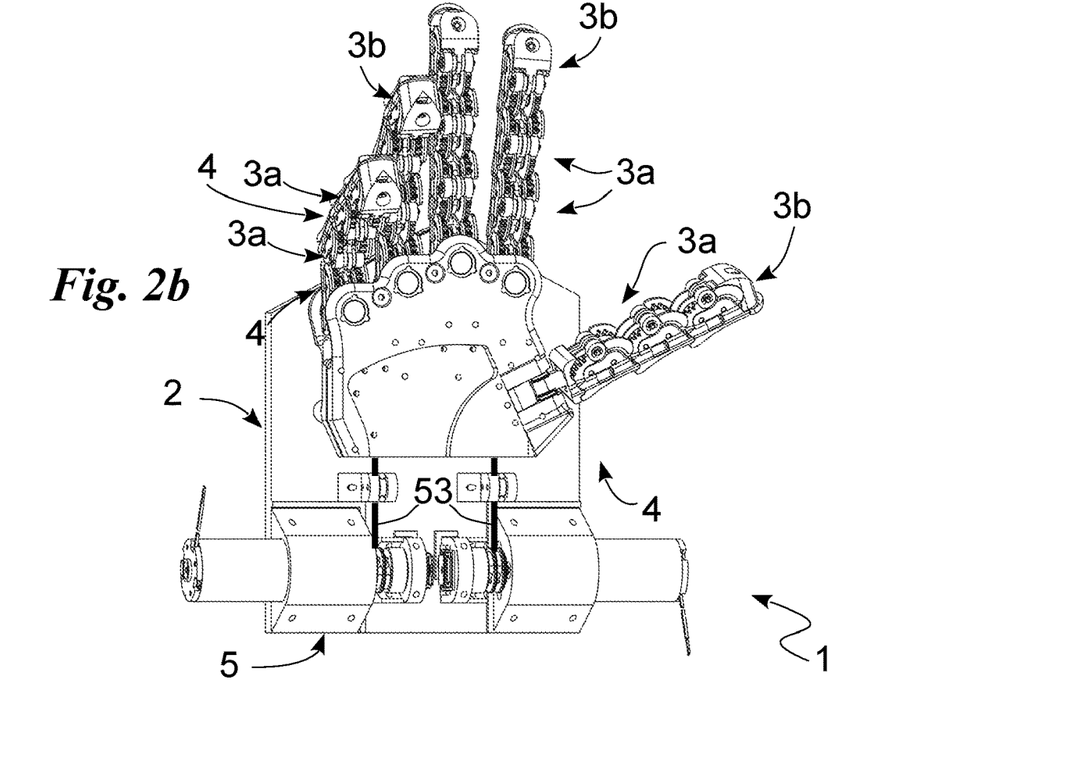
Figure 2C:
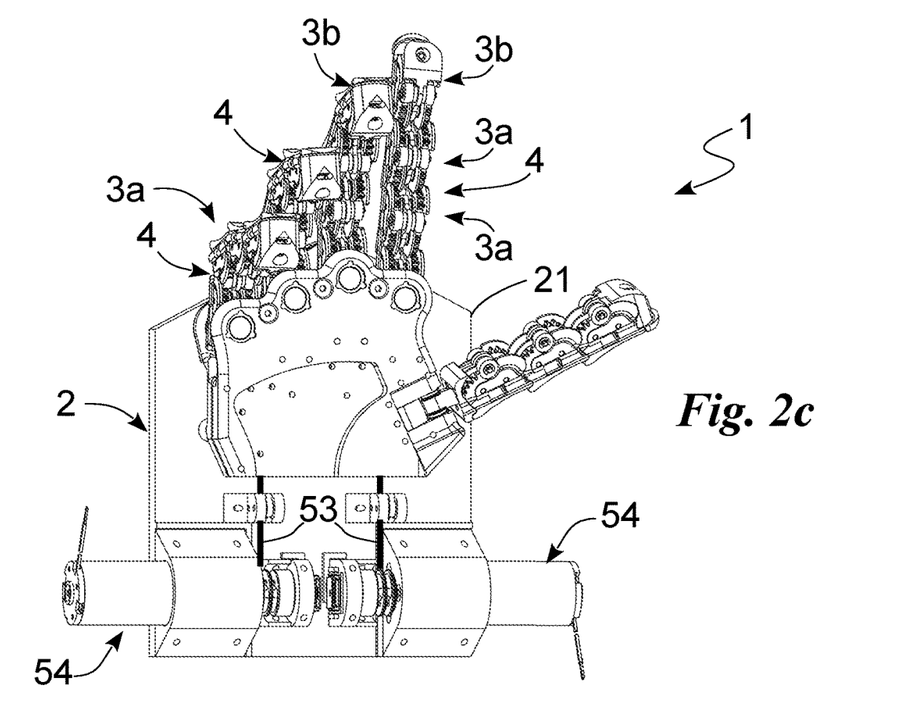
Figure 2D:
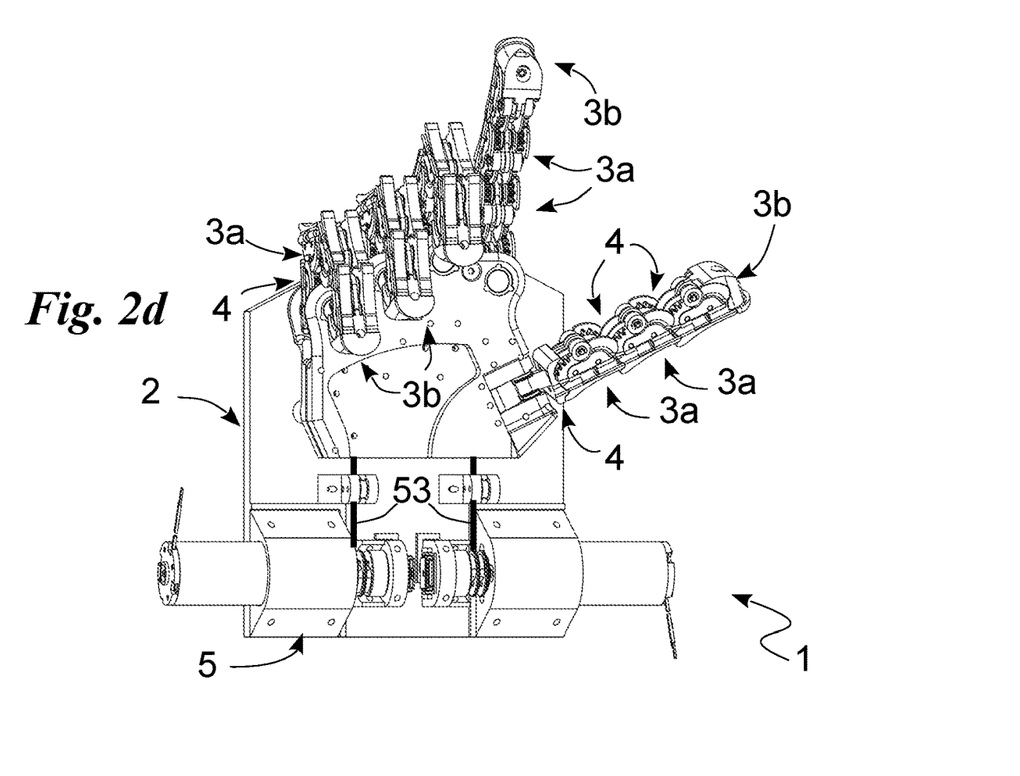

In a second example, only a single motor 54 is supposed to be activated, while the other is maintained fully blocked (so that it can counteract the tension of the cable without moving), thereby causing a tension distribution along the entire path of the cable 53 which will entail an initial movement of the phalanges 3a and/or 3b close to the active motor 54 and only later a subsequent movement of the remaining phalanges 3a and 3b (first, according to the kinematic chain, the ones closest to the active motor 54). This example of proportional and sequential closure is shown in FIGS. 2a-2d, while the final pose obtained is illustrated in FIG. 2d.

By applying a different force/torque at the two ends of the cable 53, initially, a transitional phase of tension distribution along the cable 53, and then a sequential activation of the pulleys 51 and 52, occur; and, only later, a steady-state phase will occur in which the tension will be distributed along the entire cable 53 and all the pulleys 51 and 52 are active, and therefore all the phalanges 3a and 3b are moving. In the transitional phase, the tension of the cable 53 causes a sequential activation of the pulleys 51 and/or 52 according to the order of the pulleys 51 and/or 52 along the kinematic chain and with accelerations/speeds proportional to the friction of the pulleys 51 and/or 52. In detail, each pulley 51 and/or 52 starts moving driven by a torque generated by the residual tension of the cable 53, i.e. by the tension applied by the motor to the cable 54 deprived of the tension drops caused by the different torques absorbed by the preceding pulleys 51 and 52, according to said kinematic chain, to said pulley 51 and/or 52 that is about to be moved.

Therefore, in the second example described above and assuming we have a cable 53 that is initially completely unloaded, the transitional phase provides that the active motor 54 stretches the portion of cable 53 adjacent to the same motor 53, only causing the movement of the pulley 51/52 closest to it (according to the order of the kinematic chain). Therefore, this pulley 51/52 starts to rotate, only at this point subjecting to tension the subsequent portion of cable 53 subtended between said pulley 51/52 and the adjacent pulley 51/52 that only now will start to move. Consequently, the pulleys 51/52 close to the inactive engine 54 will be the last to be activated, causing the proportional and sequential closure as seen in FIGS. 2a-2d.

It is obvious that by differentially activating the motors 54, i.e. by varying the tensions at the ends of the cable 53, during the transitional phase, it is possible to diversify from one another the torques acting on the individual pulleys 51 and 52, and hence modify the closure of the robotic hand 1 and give the robotic hand 1 particular handling capabilities. In fact, the control unit, appropriately subsequent to a command given by the operator, can command a first activation of the motors 53 (for example in the same way), wherein the hand 1 grasps an object, and a second activation of the motors 53 (for example with torques having a different modulus and/or direction), wherein the robotic hand 1 handles and, for example, rotates the object.

This ability to differentiate the action of the motors 53 also allows, at least in the transitional phase, for opposite movements between the phalanges 3a and 3b. In fact, supposing the fingers of the robotic hand 1 are only partially bent, by activating the motors in mutually opposite directions, in the transitional phase, the pulleys 51 and 52, and therefore the phalanges 3a and 3b proximal to a motor 54, have speeds opposite to the pulleys 51 and 52, and therefore to the phalanges 3a and 3b proximal to the other motor 54; whereas, in the steady-state phase, the pulleys 51 and 52 and the phalanges 3a and 3b move in accordance with the motor applying a higher-modulus force, or remain stationary in the case of an opposite modulus.

To further clarify this concept, we can consider the case of a rope rested on the ground and pulled from one end only. Initially (transitional phase), only the portion proximal to the end that is pulled will move, while the remaining portions of the rope will begin to move sequentially until (steady-state phase) the whole rope starts moving. On the other hand, in the case where the rope is pulled from both ends with opposite forces, initially (transitional phase), only the ends will move (each of which moves in accordance with the force applied thereto), whereas, in the steady-state phase, the whole rope will move in accordance with the greater of the two forces applied to the ends.

A further advantage is the aforesaid ease of construction due to the simplicity of the actuating mechanism 5.

It is further increased by the fact that, while the previously known robotic hands required a large number of control sensors, the robotic hand 1 requires a maximum of two sensors 55 for controlling the two motors 54.

Another advantage is that, since the robotic hand 1 can be controlled thanks to the two motors 54, an extremely simple control unit and also a low number of wires for connecting the control unit to the hand and, precisely, to the motors 54 and any sensors 55, will suffice.

Therefore, a further advantage is the smaller size of the robotic hand 1.

A major advantage is given by the special hinges 4 that, thanks to the presence of the elastic means 42, are able to maintain the phalanges 3a and 3b close to each other and in the correct position.

A no less important advantage is given by the stopper 43, which in addition to limit the angle of divergence between the first and the second element, allows said elements to be put in relation with one another. In fact, if for example two phalanges 3a and/or 3b are mutually driven apart, the elastic means will draw said phalanges close, while the teeth 431 and 432, by contacting each other, position said phalanges correctly.

Please note that in the document a "simple" rotation of the phalanges 3a and 3b was mentioned, even though in reality the phalanges 3a and 3b, due to the simultaneous presence of the hinges 4 and pulleys 51 and 52, perform a double rotation, one with an axis defined by the hinges 4 and another by the pulley 51 and/or 52 thereto associated.

The invention is susceptible of variations falling within the scope of the inventive concept, as specified in the independent claims, and of the related technical equivalents. In this context, all details are replaceable by equivalent elements and any type of materials, shapes and dimensions may be present.

The invention claimed is:

1. A robotic hand, comprising,
   a palm;
   a plurality of phalanges adapted to reproduce a plurality of fingers;
   hinges each of which hinging a first element identifying one of said phalanges to a second element identifying one among said palm and one of said phalanges distinct from said first element;
   at least one actuating mechanism, the at least one actuating mechanism comprising:
   first pulleys, each one located at each of said hinges and bound to said first element;
   second pulleys, each one located at each of said hinges and bound to said second element;
   a single cable running in all of said pulleys;
   at least two motors adapted to apply different tensions to said cable
   wherein at least one of said first pulleys and said second pulleys has a different friction so that said pulleys cause tension drops in said single cable, which are different from one another, and said single cable comprises subtended sectors between said pulleys, which have a non-homogeneous tension, giving different actuation forces to said elements and consequently different mutual rotation speeds between said elements.

2. A robotic hand according to claim 1, wherein said cable is open, defining two ends; and wherein each of said at least two motors is engaged at one of said ends of said cable.

3. A robotic hand according to claim 1, wherein said one actuating mechanism comprises two of said at least two motors.

4. A robotic hand according to claim 1, wherein said cable is open, defining two ends; and wherein each of said two motors is engaged at one of said ends of said cable.

5. A robotic hand according to claim 1, wherein said one actuating mechanism comprises a control unit adapted to control said at least two motors by varying between them the tension that each motor applies to said cable and therefore the mutual rotation speeds between said elements.

6. A robotic hand according to claim 1, wherein, said actuating mechanism comprises said different friction pulleys at each one of said hinges.

7. A robotic hand according to claim 1, wherein said different friction pulleys are at least partially made of different materials.

8. A robotic hand according to claim 1, wherein said different friction pulleys have different radii.

9. A robotic hand according to claim 1, wherein each one of said hinges comprises two curved surfaces, one of which being integral with said first element and another with said second element and adapted to engage with each other, allowing for rotation between said first element and said second element; and suitably, elastic means adapted to tighten said elements relative to one another ensuring contact between said curved surfaces.

10. A robotic hand according to claim 9, wherein said elastic means can be identified as a closed loop made of elastic material.

11. A robotic hand according to claim 1, comprising, for each one of said fingers, two phalanges proximal to said palm and positioned one after the other; and a phalanx distal to said palm.

* * * * *